(12) United States Patent
Robinson et al.

(10) Patent No.: US 6,721,604 B1
(45) Date of Patent: Apr. 13, 2004

(54) REDUCED DIAMETER, LOW RESISTANCE MEDICAL ELECTRICAL LEAD

(75) Inventors: Paul J. Robinson, Mahtomedi, MN (US); Bradley J. Wessman, Maple Grove, MN (US); Mark Gerald Schrom, Hugo, MN (US)

(73) Assignee: MicroNet Medical, Inc., White Bear Lake, MN (US)

( * ) Notice: Subject to any disclaimer, the term of this patent is extended or adjusted under 35 U.S.C. 154(b) by 247 days.

(21) Appl. No.: 09/626,631

(22) Filed: Jul. 27, 2000

(51) Int. Cl.[7] .................................................. A61N 1/05
(52) U.S. Cl. ....................................................... 607/116
(58) Field of Search ................................. 607/116, 119, 607/122–129; 600/373–381

(56) References Cited

U.S. PATENT DOCUMENTS

| | | | |
|---|---|---|---|
| 4,484,586 A | 11/1984 | McMickle et al. | 128/786 |
| 4,764,324 A | 8/1988 | Burnham | 264/786 |
| 5,324,328 A | 6/1994 | Li et al. | 607/129 |
| 5,330,521 A | 7/1994 | Cohen | 607/122 |
| 5,354,327 A * | 10/1994 | Smits | 174/117 R |
| 5,358,517 A | 10/1994 | Pohndorf et al. | 607/116 |
| 5,360,442 A | 11/1994 | Dahl et al. | 607/129 |
| 5,483,022 A | 1/1996 | Mar | 174/128.1 |
| 5,792,401 A | 8/1998 | Burnham | 264/103 |
| 5,796,044 A * | 8/1998 | Cobian et al. | 174/103 |
| 6,017,335 A | 1/2000 | Burnham | 604/282 |
| 6,400,992 B1 * | 6/2002 | Borgersen et al. | 607/122 |

* cited by examiner

*Primary Examiner*—Jeffrey R. Jastrzab
(74) *Attorney, Agent, or Firm*—Peter R. Lando

(57) ABSTRACT

The present invention provides an implantable electrical lead having a reduced diameter and a relatively low resistance. The lead includes a lead body having at least one conductor manufactured from drawn-filled-tubing and having an elongated cross-sectional shape to confer a high cross-sectional area relative to the conductors thickness. The lead body insulates the conductor from contact with the patient and in the case of a plurality of conductors isolates the conductors from one another. The lead body may also include a lumen extending from the lead body's proximal to distal ends.

18 Claims, 4 Drawing Sheets

REDUCED DIAMETER, LOW RESISTANCE MEDICAL ELECTRICAL LEAD

BACKGROUND OF THE INVENTION

1. Field of the Invention

This invention relates to a medical leads having drawn-filled-tubing (DFT) conductors and more specifically to a medical lead having a low-profile DFT conductor to creating a medical lead with a reduced diameter and low resistance.

2. Discussion of the Related Art

A variety of medical electrode catheters are available today for the diagnosis and treatment of various disorders of the cardiovascular and neurological systems. These electrode catheters can be used to sense electrical activity within the body and to deliver different forms of energy to stimulate, ablate, cauterize or pace. Examples of medical catheters using electrodes include permanent and temporary cardiac pacing leads, electrophysiologic (EP) catheters, electrocautery probes and spinal stimulation catheters.

Conventional neural stimulation therapies rely on neurostimulation leads for stimulating various regions of the spinal cord that correspond to each physiologic region of the body. Placement of leads for both external and implantable RF stimulating devices is relatively simple for spinal cord stimulation. Here, a Tuohy needle is inserted into the spinal epidural space and the leads are placed adjacent to the targeted nerves addressing a specific painful region of the body. A relatively high power must be applied when directly stimulating the spinal nerves compared to the power required for peripheral nerve stimulation and deep brain stimulation. The high power consumption increases the frequency of the surgeries required for battery replacement. Thus, battery life is a major limitation for totally implantable systems. The relatively high resistance of conventional reduced diameter leads further increases the power necessary for spinal stimulation and further decreases the battery's life. Therefore, a need exists for a lead body that more efficiently conducts electricity to reduce power consumption.

Further, spinal cord stimulation has limited effectiveness for certain pain conditions primarily due to limited accessibility to targeted nerves. In many cases where spinal cord stimulation is inadequate, spinal or peripheral nerves must be specifically stimulated to provide pain relief However, with existing technology, access to certain nerves can only be accomplished by a laminectomy, a surgery removing a portion of a vertibrae's lamina, which results in significant scarring and patient discomfort. Therefore, a need exists for a lead that provides increased accessibility to perform a broader array of nerve stimulation.

Procedurally, spinal or peripheral nerve stimulation is more challenging than spinal chord stimulation. The spinal and peripheral nerves branch off of the spinal chord through the transverse foramen of the vertebrae. Spinal and peripheral nerve stimulation is necessary when a region of the body is affected that cannot be effectively stimulated via the spinal cord. To stimulate these nerves, a lead is inserted through the epidural space along the spinal chord and then turned laterally outward to track the branching nerves. To track these nerves requires a lead having a significantly smaller diameter than conventional stimulation leads. Therefore, a need exists for a reduced diameter lead to access the spinal and peripheral nerves.

The higher resistance of conventional reduced diameter leads also limits cardiac pacing, mapping and ablation catheters. Available reduced diameter leads may provide access to location within the heart and veins that would not otherwise accessible, but currently available leads do not provide the advantage of combining reduced diameter with reduced resistance. The advantages for cardiac pacing of reduced size include more efficient valve function when the lead passes through the valves in the heart and better access to smaller veins without compromising blood flow. Further, the reduced resistance provides the advantage of reducing the frequency of battery changes in the pacemaker. Thus, a need exists for a low resistance reduced diameter lead.

Sensing, in both cardiac and neurological applications, can be limited by the ability to effectively transmit signal from the patient to the medical device. Sensed events typically produce very week signals. Therefore, because of their higher resistance, conventional reduced diameter leads may limit the sensitivity of reduced diameter sensing leads. Thus, a need exists for a reduced diameter lead having lower resistance for application to neurological and cardiac sensing.

Conventional reduced diameter leads typically employ ribbon wire having a rectangular cross-section as conductors. These ribbon wire conductors provide adequate cross-sectional area for reduced resistance while maintaining a sufficiently low profile to reduce the overall diameter of the lead. These ribbon wires are typically solid stainless steel, MP35N, platinum/iridium, titanium and other biocompatible metals and alloys known to those skilled in the art. Although sufficient in most applications, these leads suffer from greater power consumption, as discussed above. Conventional leads have used DFT conductors at least in part for their reduced resistance relative to the above listed metals. The DFT previously used for leads has had a round cross-section, but the round cross-section limits the minimum size for a lead body's construction. Thus, a need exists for a low-resistance lead body having a reduced profile.

The present invention meets the above needs and provides other improvements and advantages that will be recognized by those skilled in the art upon review of the following description and drawings.

SUMMARY OF THE INVENTION

A lead body in accordance with the present invention has a reduced diameter while retaining low resistance relative to a conventional reduced diameter lead. The low resistance of a lead in accordance with the present invention minimizes power consumption resulting in longer battery life and less frequent surgical interventions. The reduced diameter of a lead in accordance with the present invention allows access and reduces the steric hindrance created by having an implanted lead.

A lead body for a medical lead having an insulator and at least one low-profile drawn-filled-tubing conductor realizes the above improvements and advantages as well as other improvements and advantages. The lead body may include one or more lumen extending along its longitudinal axis. The low-profile drawn-filled-tube conductors are typically spirally wound within the insulator. Thus, the conductors are electrically insulated from one another within the lead body. The conductors typically extend from the distal end to the proximal end of the lead body. The conductors are typically electrically connected to one or more electrodes positioned toward the lead's distal end. The conductors are typically electrically connected to one or more connector pins at the lead's proximal end.

The low-profile drawn-filled-tubing conductors are composed of an outer casing and a core material. The low-profile drawn-filled-tube conductor typically has a cross-sectional shape that is crescent shaped, oval, trapezoidal, rectangular or similar low-profile cross-sectional shape. The outer casing is composed of stainless steel, MP35N, titanium, elgiloy or other suitable material. The core material is silver, gold, platinum. tungsten, tantalum copper or other suitable conductive material.

The method of the present invention provides an improved method for fabricating electrical stimulating leads. The lead body can, if desired, retain a central lumen through which a guidewire or stylet may pass. The present invention further provides a method for constructing a low resistance, leads of relatively small diameters. The method comprises heating an insulating material and embedding at least one low-profile drawn-filled-tubing conductor in the insulating material. By using the low-profile drawn-filled-tube conductor, the construction minimizes outside diameter and maximizes inner lumen space for over-the-wire delivery, stylet insertion, infusion of fluids, additional conductors and steering systems. The resulting leads provide enhanced sensitivity to low-level signals, providing improved output clarity and lower energy requirements when delivering stimulating currents to selected nerve tissue.

DETAILED DESCRIPTION OF THE INVENTION

The present invention provides a lead body of the type typically used in medical leads. The invention is described generally in the context of a neurostimulating lead as a specific example for illustrative purposes only. The appended claims are not intended to be limited to any specific example or embodiment described in this patent. It will be understood by those skilled in the art that the lead of the present invention may be used for a wide variety of applications with only insubstantial changes to the apparatus and method, described below. These applications include, but are not limited to, spinal stimulation, peripheral nerve stimulation, deep brain stimulation, neuromonitoring, cardiac monitoring, cardiac rhythm management, ablation, mapping, or other medical applications using leads. Further, the numbering of elements is repeated throughout the drawings where the elements are substantially the same or perform the same function.

Figure 1:
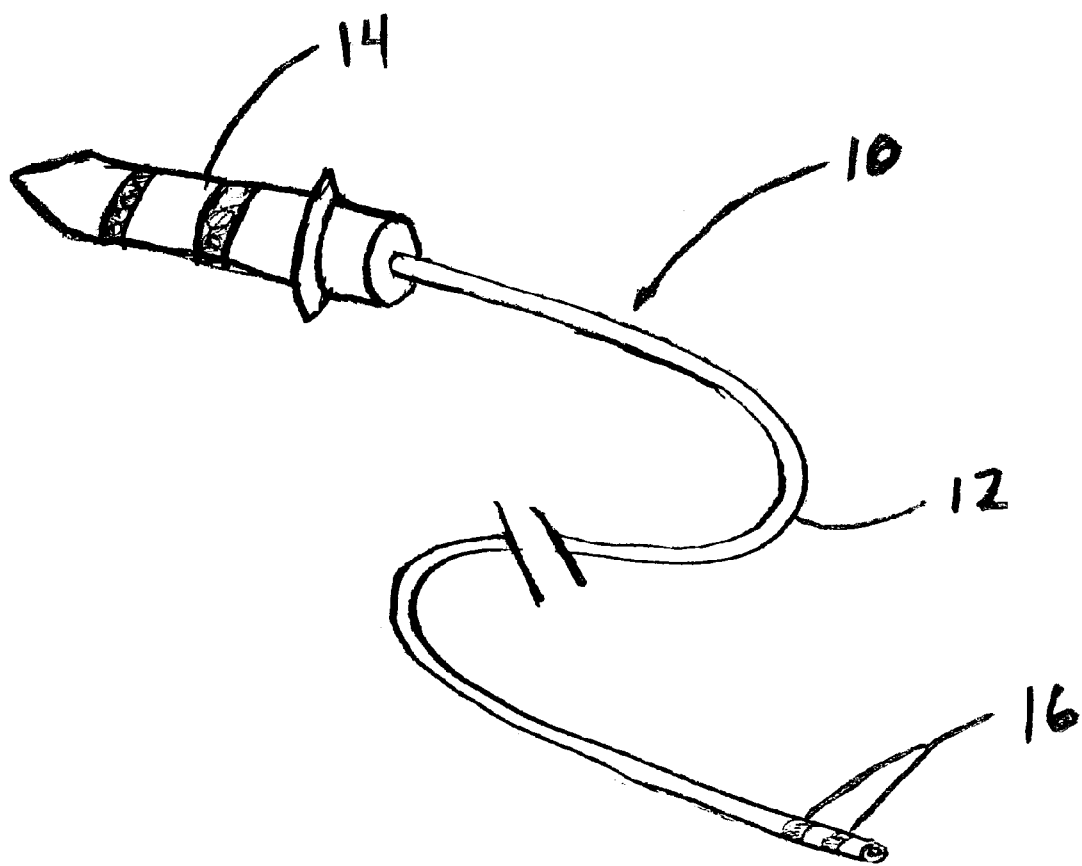
FIG. 1 illustrates a perspective view of a lead in accordance with the present invention.
Figure 2A:
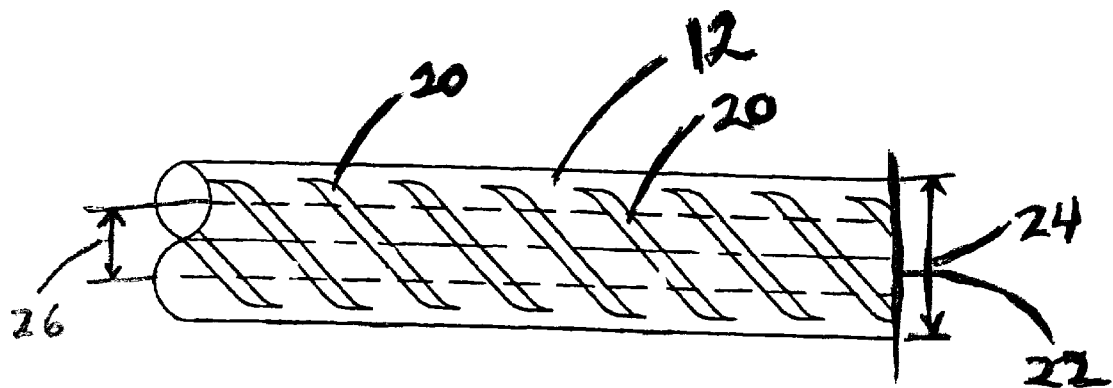
FIG. 2A illustrates a longitudinal cross-sectional view of a section of a lead body in accordance with the present invention.
Figure 2B:
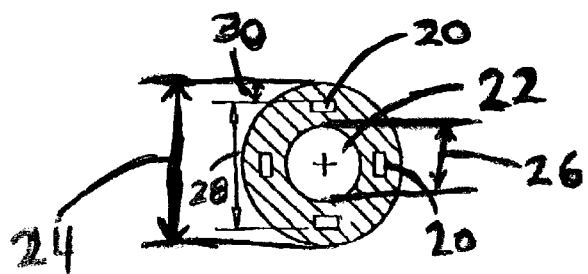
FIG. 2B illustrates an end view of a lead body having four conductors in accordance with the present invention.

Referring to FIG. 1, a lead 10 in accordance with the present invention is shown. Lead 10 includes a lead body 12, at least one connector pin 14 and at least one electrode or sensors 16. One or more conductors 20, shown in FIGS. 2A and 2B, are embedded in the lead body 12 and electrically couple the connector pin 14 to the electrodes 16. Connector pin 14 is typically connected to the lead body at the lead body's proximal end. Electrodes and/or sensors 16 are typically connected at or near the lead body's distal end.

Typically, lead body 12 electrically isolates conductors 20 from the patient when the lead is implanted. In addition, lead body 12 may isolate conductors 20 from one another when there are a plurality of conductors 20 connected to a plurality of electrodes or sensors 16. One or more lumen 18 may also be provided through the lead body 12. Lumen 18 typically extends from a proximal end 14 to a distal end 16 of the lead body. Connector pin 14 may have a central lumen coextensive with lumen 18. Lumen 18 allow a guidewire or stylet to pass for over-the-wire placement of the lead, for drug delivery, for steering wires or for other purposes that will be recognized by those skilled in the art.

Lead body 12 also typically provides the biocompatible surface for implantation. Lead body 12 is formed from at least one flexible insulating material that will be recognized by those skilled in the art. Typically the material is a medical grade polymer having at least the outermost material being biocompatible. A variety of suitable polymers may be used, including but not limited to silicone, polyurethane, polyethylene, polyimide, PTFE, and ETFE. Other polymers and other materials suitable will be recognized by those skilled in the art fall within the scope of the present invention.

Referring to FIGS. 2A and 2B, the particular dimensions for a lead body in accordance with the present invention are dictated by the lead body's final application. For exemplary purposes, the outside diameter 24 of lead body 12 for use in neurostimulation lead may be 0.01 to 0.065 inch. Typically, a lead having a lumen 22 in accordance with the present invention for use in neurostimulation applications can have a lumen diameter 26 of around 0.012 inch and an outside diameter 24 of around 2 French. Further, the reduction in the outside diameter 28 between diametrically opposed conductors due to the use of the low-profile conductors is most evident in the cross-section shown in FIG. 2B. Conductors 20 are shown in a rectangular cross-section minimizing the conductor diameter 28 while retaining an insulating layer 30 sufficient to electrically isolate conductor 26 from the patient. Thus, the reduction of outside diameter 28 allows for the reduction of lead body diameter 24 while maintaining an appropriate insulation thickness between the conductors and the patient.

FIG. 2A shows four conductors spirally wound in parallel within the material of lead body 12. Typically the conductors are spirally wound within the lead body to impart a greater amount of flexibility to the lead. The conductors may be alternatively configured within lead body 12 to impart additional physical characteristics governed by conductor configuration, as will be recognized by those skilled in the art. The characteristics may include steerability, limited flexibility, as well as other characteristics. FIG. 2A shows the low-profile conductors 26 spirally wound and they extend from the proximal end 14 to the distal end 16 of the tubular catheter body 12. The spiral winding is typically such that each of the conductors 20 is physically spaced from an adjacent conductor 20 and in that they are electrically insulated from one another within the lead body 12.

Figure 3:
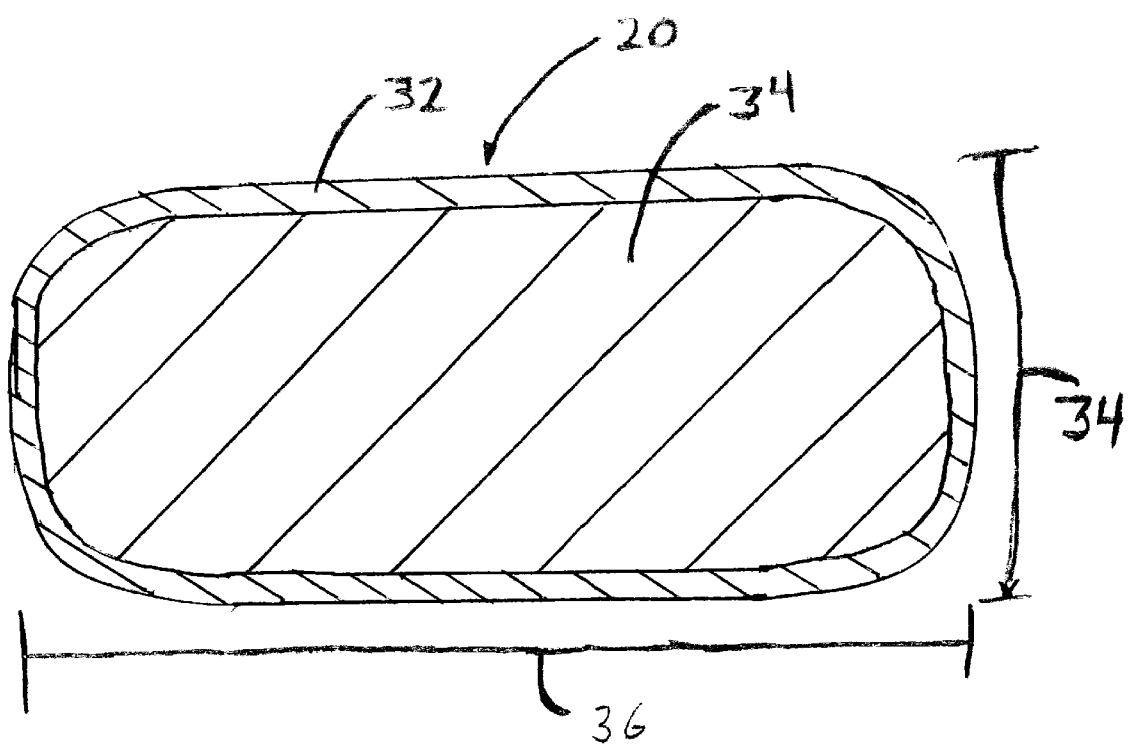
FIG. 3 illustrates a greatly enlarged cross-sectional view of a DFT conductor in accordance with the present invention.
Figure 4A:
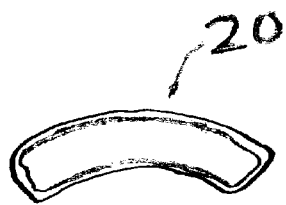
FIGS. 4A–4D illustrate a variety of cross-sectional shapes for DFT conductors in accordance with the present invention.
Figure 4B:
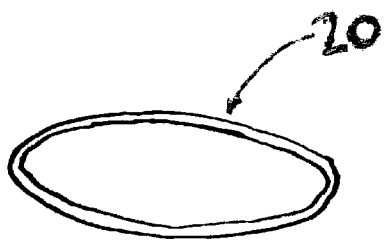
Figure 4C:
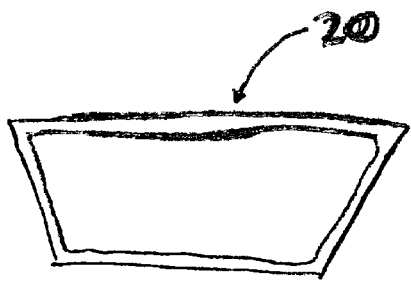
Figure 4D:
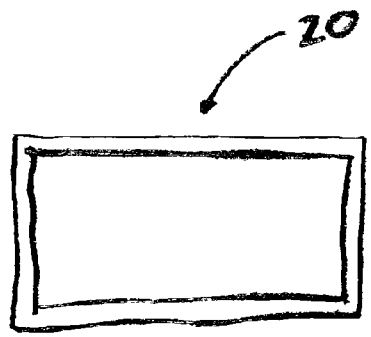

FIG. 3 illustrates a cross-section of a conductor 20. Conductors 20 used in lead bodies in accordance with the present invention are a drawn-filled-tubing (DFT). DFT includes an outer casing 32 filled with a low-resistance conductive core 34. Typically, casing 32 is composed of stainless steel, MP35N, elgiloy, titanium, or of other materials that will be recognized by those skilled in the art. The conductive material 34 is typically silver, gold, platinum, tungsten, tantalum, copper or alloys including these metals when the primary purpose is for increased conductivity. Gold, tungsten, tantalum, platinum-iridium, platinum or alloys including these metals may be used for increasing the radiopacity of the DFT.

Conductors 20 in accordance with the present invention are a DFT having a generally oval, rectangular or otherwise elongated cross-sectional shape. The low-profile shape is selected to maximize the cross-sectional area while reducing the profile or thickness 34 of the conductor Conductors 20 may have their casings 32 extruded with the desired low-profile shape or the conductor 20 may be manufactured into the desired shape by passing conventional round DFT between a pair of appropriately space rollers. FIGS. 4A, 4B, 4C and 4D illustrate crescent, oval, trapezoidal and rectangular shapes, respectively, of conductors in accordance with the present invention.

For the present invention, the low-profile DFT is configured with a thickness 34 to width 36 ratio of less than 4:5. Typically, the ratio is 1:2 or lower. For example, a rectangular conductor used in neurostimulation leads may measure 0.002 inch thick and 0.004 inch wide. The advantage of changing the shape of the conductors from round to rectangular, oval or an otherwise elongated shape is readily apparent below in Table 1. Table 1 compares the relative thickness of conductors for a range of rectangular proportions to circular conductors with both configurations having the same cross sectional area.

TABLE 1

| Rectangular Proportion – Thickness:Width | Circular Diameter – Thickness |
| --- | --- |
| 1:2 | 1.60 |
| 1:3 | 1.95 |
| 1:4 | 2.26 |
| 1:5 | 2.52 |

Table 1 demonstrates a significant reduction in thickness for the rectangular cross section while retaining the same cross sectional area. That is, to achieve a similar resistance using DFT in a conventional configuration versus a 2:1 width to thickness ratio would require a diameter (thickness) 60% larger than the equivalent conductor in accordance with the present invention.

Table 2 compares of the combined effect of composition and configuration on the resistance of conductors in accordance with the present invention with typical conductors used in lead construction. The table presupposes that the conductors of the various compositions all have the same length.

TABLE 2

| | Relative Resistance (unitless) | Relative Area (sq. in.) | Rectangular Wire (T:W = 1:2) | | Round Wire |
| --- | --- | --- | --- | --- | --- |
| | | | Thickness (inches) | Width (inches) | Diameter (inches) |
| DFT (MP35N/ 45% Ag) | 0.86 | 6.880E–06 | 0.0019 | 0.0037 | 0.0030 |
| DFT (MP35N/ 41% Ag) | 1 | 8.000E–06 | 0.0020 | 0.0040 | 0.0032 |
| DFT (MP35N/ 33% Ag) | 1.18 | 9.440E–06 | 0.0022 | 0.0043 | 0.0035 |
| DFT (MP35N/ 28% Ag) | 1.41 | 1.128E–05 | 0.0024 | 0.0047 | 0.0038 |
| DFT (MP35N/ 25% Ag) | 1.55 | 1.240E–05 | 0.0025 | 0.0050 | 0.0040 |
| DBS | 2.86 | 2.288E–05 | 0.0034 | 0.0068 | 0.0054 |
| Pt/Ir (90/10) | 6.818 | 5.454E–05 | 0.0052 | 0.0104 | 0.0083 |
| Ti | 11.5 | 9.200E–05 | 0.0068 | 0.0136 | 0.0108 |
| SS (304 or 316) | 20.45 | 1.636E–04 | 0.0090 | 0.0181 | 0.0144 |
| MP35N | 28.23 | 2.258E–04 | 0.0106 | 0.0213 | 0.0170 |

The first vertical column (from left to right) lists the materials commonly used as conductors in lead bodies. Each column is normalized to the second horizontal column the DFT having a casing composed of MP35N and a core material of 41% Ag. The second vertical column illustrates the relative resistance of the conductors assuming the same cross-sectional area for all conductors. The third vertical column illustrates the cross-sectional area necessary to achieve the same electrical resistance. The fourth and fifth vertical columns show the dimensions for thickness and width, respectively, to achieve the area shown in the third column. The sixth vertical column shows the diameter (thickness) necessary for a round wire to have the same area as provided in the third column for comparison. Table 2 demonstrates the advantages of combining the materials and configuration of the present invention.

A variety of methods recognized by those skilled in the may be used to manufacture of a lead body in accordance with the present invention. The following methods are provided for illustrative purposes only and are not intended to limit the scope of the present invention. As illustrated in the above-described figures, the leads are typically manufactured with spirally wound conductors to confer flexibility and other desired physical characteristics on the lead body. When spirally wound, the pitch of the spiral windings may be such that the turns are at an angle of between about 10 to about 80 degrees to the longitudinal axis of the lead body. The possible range for pitch is directly dependent on the number of electrodes and therefore the number of conductors 20 in the lead body. Alternatively, the conductors could be embedded in the lead body in non-spiral configurations. The following exemplary methods set forth potential methods for manufacturing a lead body in accordance with the present invention.

A first method is described in U.S. Pat. Nos. 4,764,324, 5,792,401 and 6,017,335 issued to Burnham (the "Burnham patents"), the disclosures of which are hereby incorporated by reference. In the Burnham patents, the lead body's material is passed through a die to extrude the lead body. Typically, the lead body is extruded over a core rod or mandrel. The extruded lead body is then pre-heated and the desired number of conductors 26 are spirally-wound around the lead body. The lead body with conductors is then passed through a die to position the conductors. Tension is then applied to the conductor to embed the conductors 26 in the tubing wall. Subsequently, the outer surface of the lead body is smoothed and/or sized by passing it through a heated dye to effectively remove any deformations created when the conductors 20 are embedded within the lead body. Once the lead body with the embedded conductors 26 is completed, the mandrel may be removed and the lead body cut to a desired length.

A second method is described in U.S. Pat. No. 4,484,586 issued to McMickle et al (the "McMickle patent"), the disclosure of which is hereby incorporated by reference. In the McMickle patent, the lead body's material is passed through a die to extrude the lead body. Typically, the lead body is extruded over a core rod or mandrel. The desired number of conductors 26 are positioned adjacent the lead body. Then a second layer is extruded over the conductors and first extruded lead body to insulate the conductors and form a biocompatible outer surface. Once the lead body with the embedded conductors 26 is completed, the mandrel may be removed and the lead body cut to a desired length.

In a third method, the lead body's material is passed through a die to extrude the lead body. Typically, the lead body is extruded over a core rod or mandrel. The desired number of conductors 20 are positioned adjacent the lead body. Then a second layer is extruded over the conductors and first extruded lead body to insulate the conductors and form a biocompatible outer surface. Subsequently, the outer surface of the lead body is smoothed and/or sized by passing it through a heated dye. Once the lead body with the embedded conductors 26 is completed, the mandrel may be removed and the lead body cut to a desired length.

In a fourth method, the lead body's material is passed through a die to extrude the lead body. Typically, the lead body is extruded over a core rod or mandrel. The desired number of conductors 26 are positioned adjacent the lead body. Then a second layer is extruded over the conductors and first extruded lead body to insulate the conductors and form a biocompatible outer surface. Subsequently, the outer surface of the lead body is smoothed and/or sized by passing it through a centerless grind. Once the lead body with the embedded conductors 26 is completed, the mandrel may be removed and the lead body cut to a desired length.

Again, the above listed exemplary methods are not intended to limit the scope for manufacture of the present invention. Further, this invention has been described in considerable detail in order to comply with the patent statutes and to provide those skilled in the art with the information needed to apply the novel principles and to construct and use such specialized components as are required. However, it is to be understood that the invention can be carried out by specifically different equipment and operating procedures, can be accomplished without departing from the scope of the invention itself.

What is claimed is:

1. A reduced-diameter low-resistance lead body for a medical lead, comprising:
   an insulator; and
   at least one low-profile drawn-filled-tubing conductor including an outer casing and a core material, the conductor having a crescent shaped cross-section.

2. A lead body, as in claim 1, wherein the at least one low profile drawn-filled-tube conductor is spirally wound within the insulator.

3. A lead body, as in claim 1, further comprising a plurality of low profile drawn-filled-tube conductors spirally wound within the insulator.

4. A lead body, as in claim 1, wherein the outer casing is comprised of a metal selected from the group consisting of stainless steel, MP35N, titanium, and elgiloy.

5. A lead body, as in claim 1, wherein the core material includes a conductive metal selected from the group consisting of silver, gold, platinum, tungsten, tantalum and copper.

6. A lead body, as in claim 1, further comprising at least one lumen extending along a longitudinal axis of the lead body.

7. A reduced-diameter low-resistance lead body for a medical lead, comprising:
   an insulator; and
   at least conductor having a crescent shaped cross-section.

8. A lead body, as in claim 7, wherein the conductor comprises a drawn-filled tubing conductor having an outer casing and a core material.

9. A lead body, as in claim 8, wherein the at least one drawn-filled-tube conductor is spirally wound within the insulator.

10. A lead body, as in claim 8, further comprising a plurality of drawn-filled-tube conductors each having an elongated cross-sectional shape and spirally wound within the insulator.

11. A lead body, as in claim 8, wherein the outer casing is comprised of a metal selected from the group consisting of stainless steel, MP35N, titanium, and elgiloy.

12. A lead body, as in claim 8, wherein the core material comprises a conductive metal selected from the group consisting of silver, gold, platinum, tungsten, tantalum and copper.

13. A lead body, as in claim 8, further comprising at least one lumen extending along a longitudinal axis of the lead body.

14. A lead body for a medical lead, comprising:
   an insulator;
   a first conductor having a crescent cross-sectional shape; and
   a second conductor electrically isolated from the first conductor and having a crescent cross-sectional shape.

15. A lead body, as in claim 14, wherein the first conductor and second conductor are spirally wound within the insulator.

16. A lead body, as in claim 14, wherein the first conductor and second conductor are drawn-filled-tube conductors each having an outer casing and a core material.

17. A lead body, as in claim 16, wherein the outer casing is comprised of a metal selected from the group consisting of stainless steel, MP35N, titanium, and elgiloy.

18. A lead body, as in claim 16, wherein the core material comprises a conductive metal selected from the group consisting of silver, gold, platinum, tungsten, tantalum and copper.

* * * * *

UNITED STATES PATENT AND TRADEMARK OFFICE
CERTIFICATE OF CORRECTION

| | | |
|---|---|---|
| PATENT NO. | : 6,721,604 B1 | |
| APPLICATION NO. | : 09/626631 | |
| DATED | : April 13, 2004 | |
| INVENTOR(S) | : Paul J. Robinson, Bradley J. Wessman and Mark Gerald Schrom | |

It is certified that error appears in the above-identified patent and that said Letters Patent is hereby corrected as shown below:

Column 8, claim 7, line 15, insert -- one -- before the term "conductor".

Signed and Sealed this

Seventh Day of November, 2006

JON W. DUDAS
*Director of the United States Patent and Trademark Office*